United States Patent [19]

Suzuki et al.

[11] 4,350,763

[45] Sep. 21, 1982

[54] METHOD FOR DETERMINING BIOCHEMICAL OXYGEN DEMAND

[75] Inventors: Shuichi Suzuki, Tokyo; Isao Karube, Tachikawa, both of Japan

[73] Assignee: Ajinomoto Company, Inc., Tokyo, Japan

[21] Appl. No.: 138,121

[22] Filed: Apr. 7, 1980

Related U.S. Application Data

[63] Continuation of Ser. No. 889,282, Mar. 23, 1978, abandoned, which is a continuation-in-part of Ser. No. 840,650, Oct. 11, 1977, abandoned.

[51] Int. Cl.³ ............................................. C12Q 1/29
[52] U.S. Cl. ............................................ 435/29; 435/4; 435/34; 435/39; 435/288; 435/291; 435/817
[58] Field of Search ..................... 435/4, 29, 288, 291, 435/817

[56] References Cited

U.S. PATENT DOCUMENTS

| | | | |
|---|---|---|---|
| 3,403,081 | 9/1968 | Rohrback et al. ................ | 435/4 X |
| 3,645,852 | 2/1972 | Axen et al. ........................ | 435/181 |
| 3,838,011 | 9/1974 | Hagen et al. ..................... | 435/4 X |
| 3,972,776 | 8/1976 | Uieth et al. ...................... | 435/177 |
| 4,073,692 | 2/1978 | Ciaccio et al. ................... | 435/29 X |

OTHER PUBLICATIONS

Leland Clark, Jr. and Champ Lyons, Electrode Systems for Continuous Monitoring in Cardiovacular Surgery, Ann. of N.Y. Acad. of Sci., vol. 102 (Oct. 1), pp. 29–45, 1962.

*Primary Examiner*—Robert J. Warden
*Attorney, Agent, or Firm*—Oblon, Fisher, Spivak, McClelland & Maier

[57] ABSTRACT

The biochemical oxygen demand (BOD) of an aqueous liquid contaminated with organic matter is determined by contacting a sample solution with elementary oxygen and with immobilized microorganisms capable of aerobically metabolizing the organic matter and of thereby consuming the oxygen. The rate of oxygen consumption under otherwise uniform conditions is as precise a measure of BOD as the conventional five-day test, but is determined within less than two hours, usually less than 30 minutes. A membrane-type oxygen-sensitive electrode is employed for sensing the rate of oxygen consumption and generates an output signal which is readily correlated with the BOD of the tested liquid.

6 Claims, 11 Drawing Figures

METHOD FOR DETERMINING BIOCHEMICAL OXYGEN DEMAND

This is a continuation of application Ser. No. 889,282, filed Mar. 23, 1978 now abandoned, which, in turn, is a continuation-in-part of application Ser. No. 840,650, filed on Oct. 11, 1977, now abandoned.

This invention relates to water analysis, and more particularly to a method and to apparatus for determining biochemical oxygen demand (BOD) in aqueous liquids containing organic matter.

While less time-consuming methods were proposed heretofore for the determination of BOD, it is still common practice to measure BOD by Standard Method No. 219 of the American Public Health Association or by the closely similar method of Japanese Industrial Standard JIS K0102-1974. Both methods require a test solution to be held under prescribed conditions for five days before the result of the test can be known, and the value of the test results depends on the skill of the operator. The need for a faster test less sensitive to human error has long been recognized, but has not yet been met.

The primary object of this invention is the provision of a method of determining BOD in an aqueous liquid which is much faster, no less precise, and less dependent on an operator's skill than the accepted standard methods. A concomitant object is the provision of apparatus for performing the method.

Many known microorganisms are capable of metabolizing aerobically organic matter in aqueous liquids, whereby elementary oxygen present in the liquid is consumed. It has now been found that the initial rate of oxygen consumption under otherwise constant conditions is proportional to the biological oxygen demand of the liquid. This rate is readily determined in a matter of less than two hours by means of equipment assembled from commercially available components, and within less than 30 minutes under most conditions. The method lends itself to automatic operation and is thus suitable for continuous monitoring of waste effluent from industrial plants and the like. Microorganisms suitable for this invention include bacteria such as *Bacillus subtilis* and *Pseudomonas aeruginosa*, molds such as *Aspergillus niger* and *Rhyzopus hormoscense*, and Actinomycetes such as *Streptomyces griseus*. Mixtures of operative microorganisms, not individually identified, are found in the active sludge of water treatment plants, in many soilds, and in organic waste materials.

They are preferably isolated from their substrates and cultured on a conventional medium from which they may be separated in a simple, known manner, as by centrifuging the broth. The number of microorganisms affects the observed rate of oxygen consumption and is not precisely reproducible. It is necessary, therefore, to immobilize an adequate number of cells, to establish the oxygen-consuming ability of the immobilized cells when in contact with solutions having known BOD, and to compare the rate of oxygen consumption of the same microorganisms in contact with an unknown test sample with a calibration chart derived from the tests on known standard samples. Because the rate of oxygen consumption is directly proportional to the BOD, a plot of BOD v. rate of oxygen consumption is represented by a straight line in a system of Cartesian coordinates.

Microorganisms may be immobilized for the purpose of this invention by trapping them between membranes or like solid bodies which are permeable to the test solution and to oxygen, but impermeable to the microorganisms, or they may be dispersed in a continuous solid matrix of a material having the same properties, such as collagen and other natural polymers or in certain synthetic resin gels known in themselves.

The aerobic metabolism of the microorganisms feeding on the organic matter present is affected by certain process variables, and the extent to which such variables are controlled affects the precision of the BOD values measured. Temperatures in excess of 50° C. unfavorably affect many microorganisms, but at lower temperatures, for example, between 15 and 40° C., their activity generally increases with the temperature. It has been found convenient to operate at a temperature slightly higher than usual ambient temperature, such as 30° C., but this temperature is not critical. Strongly acidic and alkaline liquids are no better suited for testing by the method of this invention than by the conventional standard methods, and neutralization of such solutions prior to testing is necessary. However, useful and reproducible results are obtained at constant pH values from less than 4 to more than 8. In neutral solutions, the pH may be permitted to vary between 6.5 and 7.5 without significant loss in precision.

Phosphate-bearing, aqueous liquids may be analyzed for BOD according to the invention if the microorganisms are adapted to phosphate ions in a manner also employed in the known standard tests.

Contaminants usually toxic to microorganisms are better tolerated in the method of the invention than in the standard five-day tests. No measurable effect on the test results has been found in the determination of BOD of waste waters containing one millimole per liter of the chlorides of mercury, cadmium, divalent or trivalent iron, and lead. Cupric chloride at the same concentration had a barely perceptible effect. Up to 0.2 moles per liter, sodium chloride may be present in the test solution without affecting the BOD readings, an often important advantage over the conventional standard methods.

The immobilized microorganisms may be employed for long series of tests in the method of the invention. A gradual decrease in the rate at which oxygen is consumed is compensated in a simple manner by recalibration at infrequent intervals.

In another embodiment of the present invention, the sample may be mixed with a fixed amount of oxygen which is soluble in the sample and the amounts of oxygen present in the sample before and after the period are sensed, the sensible signal being indicative of the difference between the amounts of oxygen sensed. In one further embodiment, the oxygen may be supplied to the sample prior to contacting the sample with the immobilized microorganisms and the sensible signal is generated in response to the sensed concentration of oxygen in the sample after contacting the sample with microorganisms.

Apparatus for performing the invention is shown in the appended drawing together with charts illustrating the operating characteristics of the apparatus.

Figure 1:
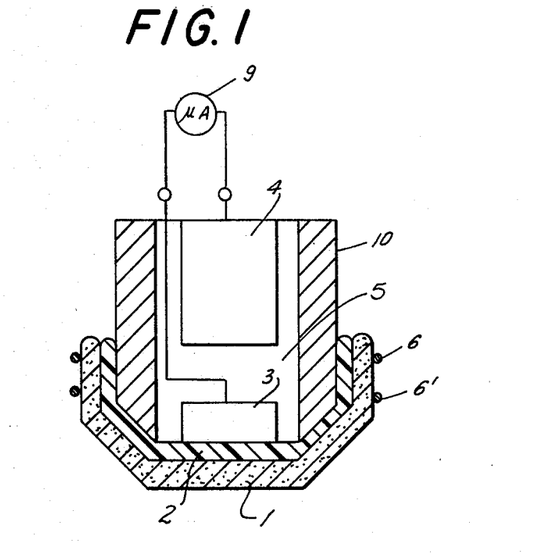
FIG. 1 illustrates a conventional, membrane-type, oxygen-sensitive electrode modified for the purpose of this invention in elevational section, the view being simplified to facilitate understanding.

Referring now to FIG. 1 in more detail, there is shown the tubular, insulating shell 10 of a conventional oxygen-sensitive electrode. One end of the shell 10 is closed by a plastic membrane 2 which is selectively permeable to oxygen. The other end of the shell 10 is also closed in a manner not shown and not relevant to this invention. A platinum cathode 3 is contiguously adjacent to the membrane 2 in the shell 10 and spaced from a lead anode 4. The cavity of the shell 10 is otherwise filled with an alkaline electrolyte 5. The electrodes 3, 4 are connected to a recording microammeter 9. The current output of the conventional electrode described so far is known to be directly proportional to the oxygen concentration at the outer face of the membrane 2. That face is covered with a layer 1 of collagen in which the cells of microorganisms are dispersed in fixed spatial relationship. The collagen film is pulled tight over the membrane 2 and held in position by two rubber rings 6, 6'.

When the modified electrode shown in FIG. 1 is immersed in waste water or the like which contains molecular oxygen, the liquid diffuses through the collagen layer in which it is stripped of some of its oxygen content as the immobilized microorganisms metabolize the organic material in the waste water. The oxygen content of the sample solution at the interface of the collagen film 1 and the membrane 2 is sensed by the electrode, and the resulting variation in the output current of the electrode is recorded on the instrument 9.

Figure 2:
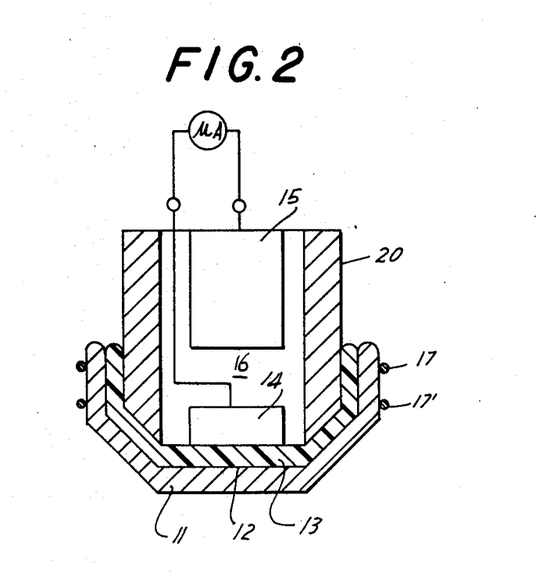
FIG. 2 shows a differently modified, known electrode of the same general type in the manner of FIG. 1.

The basically similar, conventional, oxygen-sensitive electrode illustrated in FIG. 2 has a shell 20 one end of which is sealed by a selectively permeable plastic membrane 13. The cavity of the shell 20 is filled with an electrolyte 16 as far as not occupied by a platinum cathode 14 and an aluminum anode 15. A conventional dialysis membrane 11 is fastened to the membrane 13 by rubber rings 17, 17'. A thin layer 12 of microbial cells is immobilized between the two membranes 11, 13 which are impermeable to the cells, while permitting passage of an aqueous waste liquid and of oxygen dissolved therein.

Figure 3:
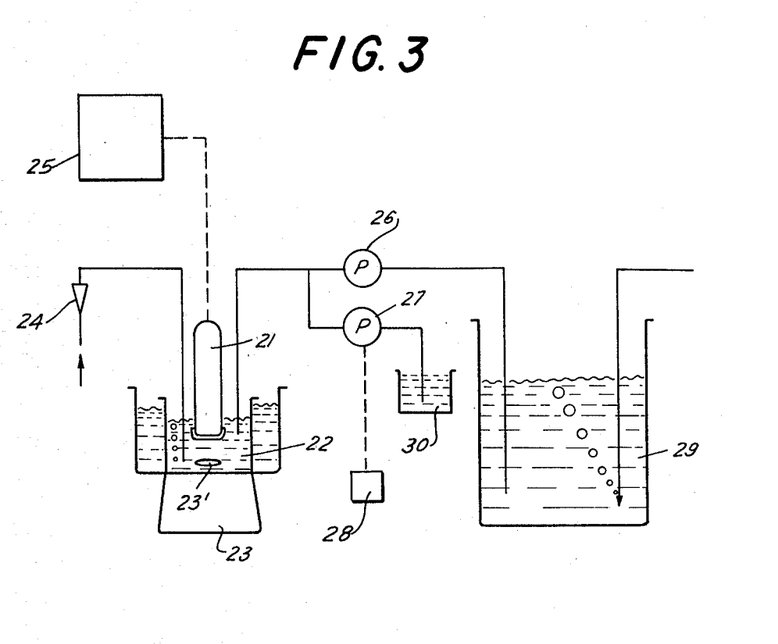
FIG. 3 is a flow sheet of equipment suitable for performing the method of the invention and including one of the electrodes of FIGS. 1 and 2.

In the BOD analysis system illustrated in FIG. 3, an oxygen-sensitive electrode 21 of one of the types shown in FIGS. 1 and 2 is partly immersed in liquid in a cell 22 whose contents may be kept at a constant temperature by the ambient air, by a jacket or by a thermostatically controlled heater in a manner well known in itself and not illustrated. The cell 22 is mounted on a magnetic stirrer 23 which turns a glass-coated steel bar 23' in the cell 22 during operation of the equipment. Oxygen may be bubbled through the liquid in the cell 22 from a non-illustrated tank through a flowmeter 24. A recording instrument 25 produces a chart of the current output of the electrode 21.

The illustrated apparatus also includes a tank 29 in which a buffer solution is kept saturated by constantly bubbling oxygen gas. A constant-output pump 26 may transfer buffer solution continuously from the tank 29 to the cell 22 from which it overflows in a manner not specifically illustrated. Another constant-output pump 27 is driven by an electric motor, not specifically shown, which is energized from time to time to inject a sample of the liquid to be tested from an interchangeable container 30 into the buffer stream.

The mode of operation of the equipment illustrated in FIG. 3 will be described hereinbelow together with FIGS. 4 to 9.

The two readings thus are in themselves a measure of the rate of oxygen consumption and of BOD.

Figure 4:
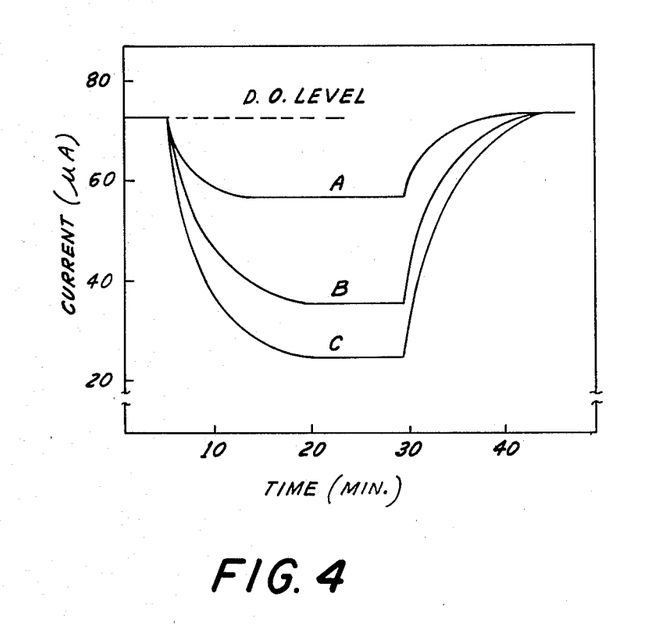
FIG. 4 shows the change of output current from the electrode of FIG. 3 over periods of less than one hour in batch operation.

The device illustrated in FIGS. 3, oxygen is continuously supplied to the interface of the liquid and the immobilized microorganisms which consume oxygen at another fixed rate. When a steady state as shown in A, B, and C or FIG. 4 is reached, the concentration of oxygen in the liquid reaches a constant equilibrium value indicative of the rate of oxygen consumption at the chosen constant oxygen supply, and thus indicative of BOD of the tested sample.

These relationships will become clearer from the following Examples which are further illustrative of this invention. In the Examples, all percentages and like values are by weight unless stated differently.

EXAMPLE 1

An electrode of the type shown in FIG. 1 was constructed and used in the following manner:

A soil extract was prepared according to the method of Japanese Industrial Standard JIS K0102-1974. 10 Ml extract was mixed with 80 ml of a culture medium containing 10% glucose, 1% peptone, 1% beef extract in tap water and having a pH value of 6.0. The mixture was cultured aerobically for 24 hours at 30° C., cooled to 5° C., and centrifuged to harvest the microbial cells which were washed twice with phosphate buffer solution (0.1 M, pH 7.0). A 1 g batch of the wet cells was suspended in 100 g aqueous 1% collagen fibrile suspension (pH 4.0) prepared according to the method of Karube et al. [Ind. Eng. Chem. Pro. Res. Develop., 10–160 (1971)]. The suspension was cast on a Teflon-coated board and dried at 20° C. The film so obtained was tanned by immersion in aqueous 0.1% glutaraldehyde solution for 1 minute at 20° C. and again dried at 4° C. Its thickness was 50 $\mu$m.

The membrane of a commercially available oxygen-sensitive electrode (Model A of Ishikawa Seisakusho, Tokyo) was covered tightly with a 2.5 cm square of the collagen film which was secured by means of two rubber rings.

A standard solution of 150 mg/l glucose and 150 mg/l glutamic acid was prepared according to the aforementioned Industrial Standard and diluted with tap water to provide standard samples having equivalent BOD values of 6, 16, and 22 ppm. Each of the three samples was tested in a portion of the apparatus shown in FIG. 3. An 80 ml aliquot of each tested solution was introduced into the cell 22 and stirred by the magnetic stirrer 23 while it was kept saturated with oxygen from the flow meter 24. The pumps 26, 27 were disconnected from the cell 22 for these tests. A uniform temperature of 30° C. was maintained. A base line (D.O. level) was established by keeping the electrode 21, prepared as described above, immersed in oxygen-saturated buffer free from oxidizable organic matter before transferring it to the cell 22.

The recorder 25 produced three curves A, B, C on the same chart shown in FIG. 4 in respective tests of the three sample. The output of the electrode dropped at a rate related to the BOD value of the tested solution to reach an equilibrium value then oxygen was consumed by the microorganisms in the collagen film as fast as it could be replenished by diffusion from the ambient saturated solution. Equilibrium at the indicated BOD values was reached within less than 20 minutes. When the test sample thereafter was replaced by phosphate buffer, the output of the electrode returned to the base line, and the next test could begin. The time required for an entire cycle was less than one hour, and not much more than 20 minutes for the most dilute sample.

Figure 5:
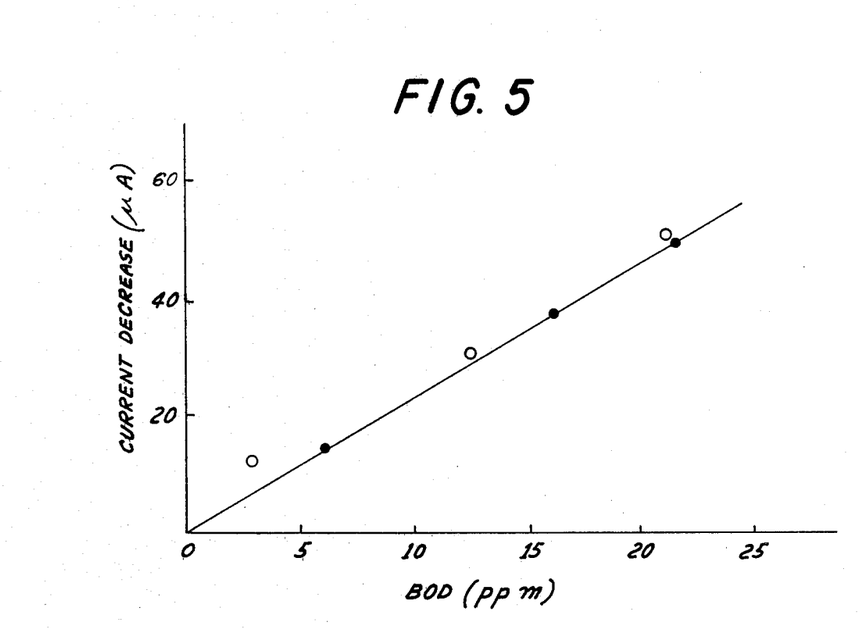
FIG. 5 is a calibration chart obtained for the apparatus of FIG. 3.

The differences between the initial blank current reading (D.O. level) and the ultimate equilibrium currents were plotted as a function of the known sample BOD (black circles in FIG. 5) and yielded a straight calibration line. The BOD of a batch of waste water from an alcohol manufacturing plant was determined in the manner described above on several diluted samples, and each sample was also tested by the conventional five-day test. Open circles in FIG. 5 show the correlation of the electrode current readings and the BOD values found by the conventional method. The conventional results agree with those that were obtained from the calibration chart as closely as can be expected from the known margin of error of the accepted conventional method.

Figure 6:
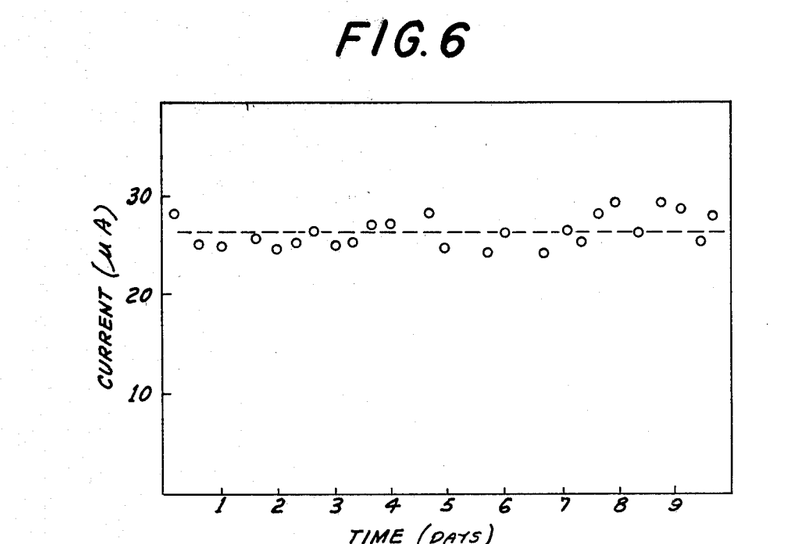
FIG. 6 graphically illustrates long-term performance of the apparatus of FIG. 3.

One of the diluted samples from the same batch of waste water was tested three times per day on ten consecutive days by the afore-described method of the invention, and the current readings so obtained are plotted in FIG. 6 (open circles). The readings indicate that the method of the invention is at least as reproducible as the conventional five-day test, and that the microbial cells immobilized in the collagen membrane remain uniformly effective for an extended time.

EXAMPLE 2

40 Ml active sludge from the waste-water purification system of a food manufacturing plant was mixed with 500 ml of an aqueous culture medium containing 1% glucose, 1% peptone, 1% yeast extract, and 0.5% NaCl (pH 6.0), and the mixture was incubated at 30° C. for 10 hours. It was then cooled to 5° C. and centrifuged for recovery of the microbial cells.

The membrane 13 of a commercial, oxygen-sensitive electrode (Oriental Denki, Japan, Type ST) was covered with a manually applied layer 12 of the wet recovered cells on filter paper which was then secured in place by means of a cellophane dialysis membrane 11 as shown in FIG. 2. The prepared electrode was installed in analysis apparatus of the type shown in FIG. 3.

Figure 7:
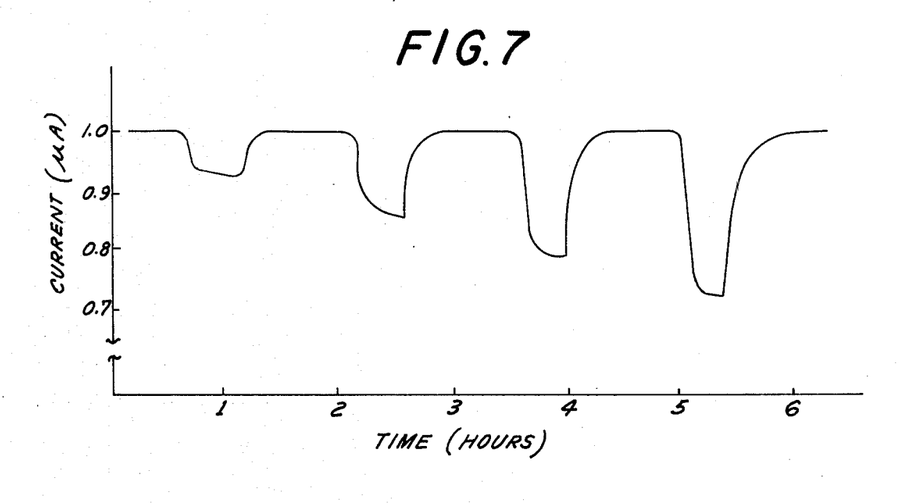
FIG. 7 is a chart of the output current from the apparatus of FIG. 3 under conditions of automatic, continuous operation.

A uniform oxygen supply to the cell 22 which had a capacity of 8 ml was maintained by feeding to the cell oxygen-saturated phosphate buffer (0.05 M, pH 7.0) from the reservoir 29 by means of the pump 26 at a constant rate of 4 ml/min. After the output reading of the electrode 21 had reached a stable value, a standard glucose-glutamic acid solution having a BOD value of 9 ppm was injected into the buffer stream from a storage vessel 30 by means of the pump 27 at a constant flow rate of 0.03 ml/min. for 30 minutes, whereupon the pump 27 was shut off by the timer 28. As is shown in FIG. 7, the current output of the electrode 21 dropped quickly, and then remained constant. When sample injection was stopped, the electrode output returned to its initial value. The procedure outlined above then was repeated with standard sample solutions having BOD values of 18, 27, and 36 ppm.

Figure 8:
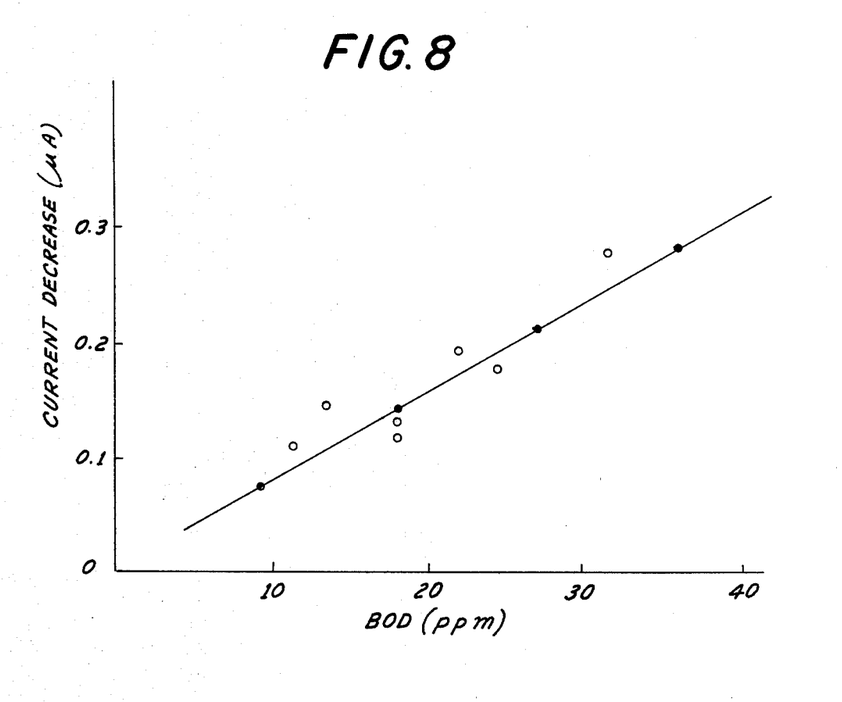
FIG. 8 is a calibration chart similar to that of FIG. 5, but for the conditions of FIG. 7.

The four values of current decrease determined in this manner were plotted against the known BOD values in FIG. 8 (black circles) to produce a straight calibration line passing through the origin of the coordinates. Waste water from the same food manufacturing plant was diluted with 0.05 M phosphate buffer (pH 7.0) to 7 different concentrations, and the samples so obtained were tested by injection into the apparatus of FIG. 3 as described above and by the standard five-day test. The relationship between the several current decrease values and the BOD values obtained in the standard tests is indicated in FIG. 8 by open circles which are located close to the calibration curve.

Figure 9:
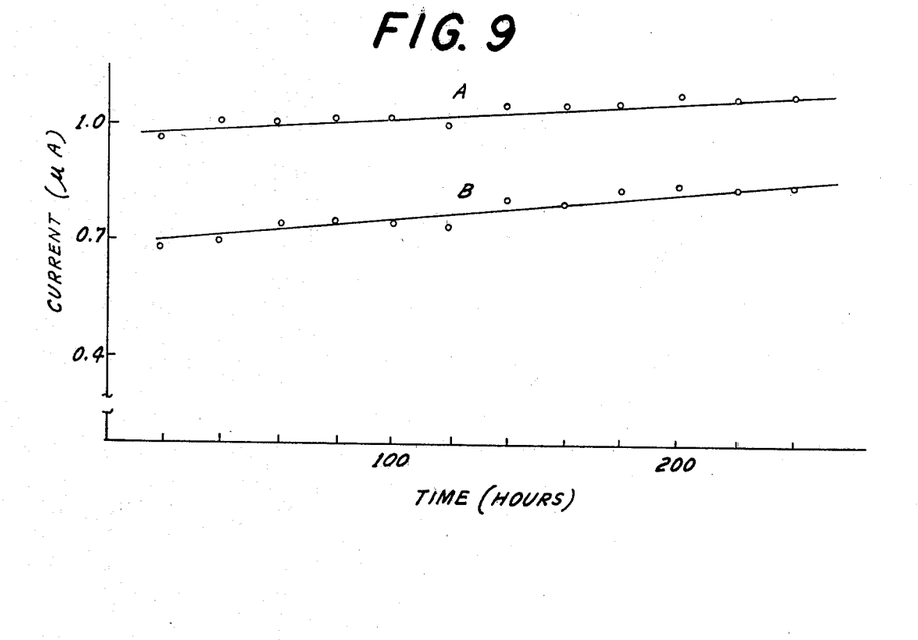
FIG. 9 illustrates long-term performance of the same apparatus in automatic operation.

The procedure described above with reference to FIG. 7 was modified to measure the electrode output in phosphate buffer solution with and without the standard 36 ppm BOD solution every 20 hours for ten days. The readings obtained are shown in FIG. 9 and are located very close to two straight lines which indicate a slight drift of both measured values, but only a minimal change in the spacing of the two lines which indicates BOD. An established calibration line showing variations of BOD with current decrease from a blank value thus remains valid over an extended period if readings of blank values are taken from time to time.

EXAMPLE 3

An electrode of the type shown in FIG. 2 was prepared as described in Example 2 and stored overnight with its membrane immersed in distilled water. A solution of glucose/glutamic acid having an equivalent BOD value of 18 ppm was prepared as described above and divided into two batches in one of which 0.16 M phosphate was dissolved.

Figure 10:
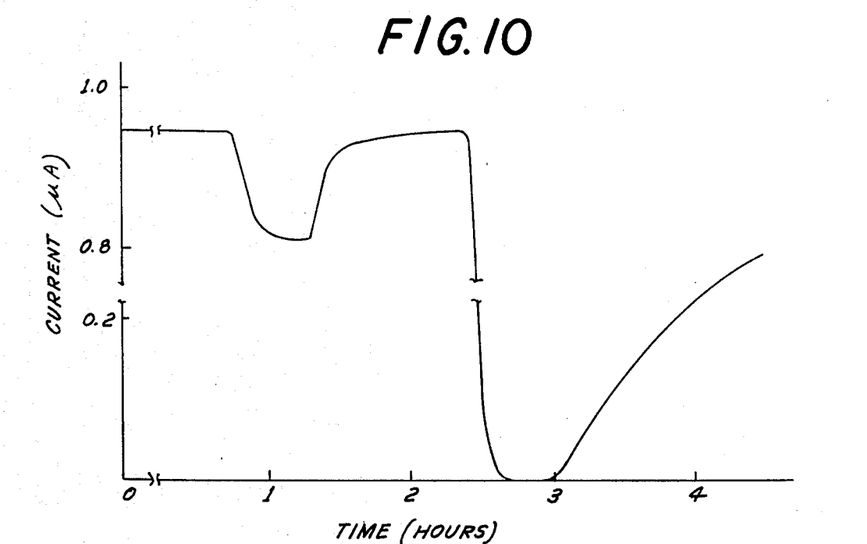
FIG. 10 illustrates the change in output current from the electrode of the type shown in FIG. 2 in the apparatus of FIG. 3 when operating on phosphate bearing-water with microorganisms not adapted to phosphate.

The output current of the electrode when immersed in distilled water was approximately 0.94 μA as is shown in FIG. 10. When the electrode was transferred to the phosphate-free standard solution, its output dropped to a fairly constant value of about 0.8 μA. It rose quite rapidly to almost the initial value when the electrode was returned to distilled water. When the electrode thereafter was dipped in the phosphate-bearing standard solution, the output current dropped practically to zero and rose only slowly toward the initial value when the electrode was returned to distilled water.

In another test run, the electrode was stored 24 hours in 0.05 M phosphate buffer (pH 6.0) for 24 hours with gentle aeration so that the endogenous respiration of the microorganisms was completely suppressed. In sequential runs on the two 18 ppm BOD samples, practically identical results were achieved with and without phosphate in the sample, as is shown in FIG. 11.

If the method of the invention is to be used on waste water containing at least 0.1 mole phosphate per liter, errors due to endogenous respiration of the microorganisms in the test system may be avoided by conditioning the microorganisms in phosphate buffer solution. Smaller amounts of phosphate in the tested liquid have negligible effects.

Figure 11:
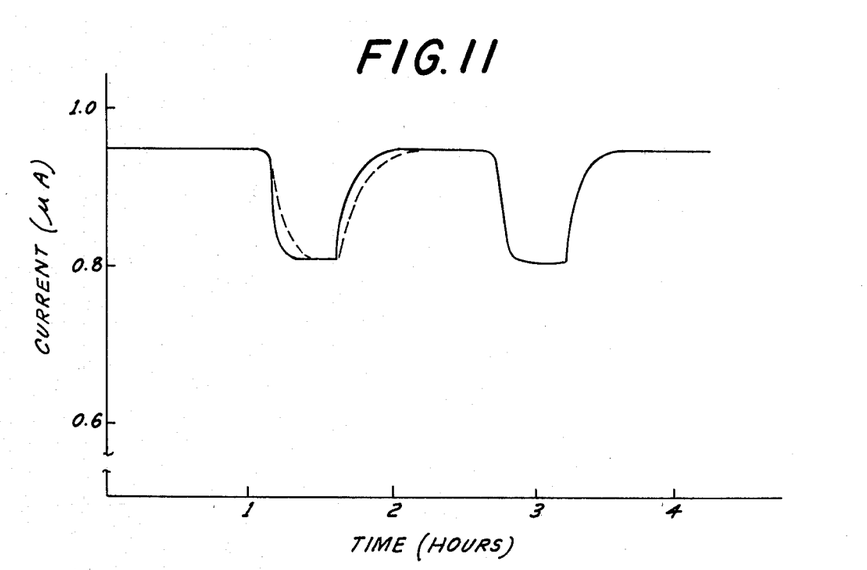
FIG. 11 is a chart analogous to that shown in FIG. 10 as obtained after adapting of the microorganisms to phosphate ions.

For comparison purposes, the first part of the curve of FIG. 10 has been superimposed in broken outline on the curve of FIG. 11. While the final equilibrium current value is the same in both cases, it is reached more quickly after phosphate conditioning of the microorganisms, as is evident from the solid line in FIG. 11.

The method of the invention has been applied in the preceding Examples to aqueous liquids having BOD values of 9 ppm (FIG. 8) to about 400 ppm (FIG. 11). However, even lower concentrations of organic matter may be determined with good accuracy, and higher concentrations are capable of being determined after dilution with clean water.

An oxygen-sensitive electrode of the membrane type is the best oxygen sensor available to us at this time. The illustrated and described electrodes are of the galvanic type, but the known electrodes of the polarographic type may be employed in an obvious manner. They are generally more sensitive to certain contaminants in the tested material and offer advantages over the galvanic type only under conditions not normally encountered in industrial practice for which this method and the apparatus of the invention are particularly useful.

Other modifications of the illustrated apparatus will readily suggest themselves to those skilled in the art on the basis of the above teachings. It should be understood, therefore, that the foregoing disclosures relates to preferred embodiments, and that it is intended to cover all change and variations of the examples herein chosen for the purpose of the disclosure which do not depart from the spirit and scope of the invention set forth in the appended claims.

What is claimed is:

1. A method of determining the biochemical oxygen demand of an aqueous liquid containing organic matter which comprises
   (a) contacting a sample of said liquid with molecular oxygen and with a microbial electrode comprising an oxygen-sensitive electrode covered by first and second membranes which are permeable to said liquid and oxygen and impermeable to microbial cells and microorganisms immobilized or confined between the membranes, said microorganisms being capable of aerobically metabolizing said organic matter and thereby consuming said oxygen,
   (b) electrochemically sensing the rate of consumption or the decrease in steady state concentration of said oxygen caused by said microorganisms during a period not exceeding two hours; and
   (8c) calculating the biochemical oxygen demand from said rate of consumption or said decrease of the oxygen by making use of the direct linear relationship between the biochemical oxygen demand and the rate of consumption or the decrease of the amount of oxygen.

2. A method as set forth in claim 1 wherein said second membrane is a dialysis membrane.

3. A method of determining the biochemical oxygen demand of an aqueous liquid containing organic matter which comprises
   (a) contacting a sample of said liquid with molecular oxygen and with a microbial electrode comprising an oxygen sensitive electrode covered by a first directly adjacent membrane and a second adjacent membrane, said membranes being permeable to said liquid and oxygen and impermeable to microbial cells and microorganisms immobilized or confined within said second membrane, said microorganisms being capable of aerobically metabolizing said organic matter and thereby consuming said oxygen,
   (b) electrochemically sensing the rate of consumption or the decrease in steady state concentration of said oxygen caused by said microorganisms during a period not exceeding two hours; and
   (c) calculating the biochemical oxygen demand from said rate of consumption or said decrease of the oxygen by making use of the direct linear relationship between the biochemical oxygen demand and the rate of consumption or the decrease of the amount of oxygen.

4. A method as set forth in claim 1 or 3 wherein said second membrane is a microbial-collagen membrane.

5. A method as set forth in claim 4 wherein said microorganisms are those which have been washed with a phosphate.

6. A method as set forth in claim 1 or 2 wherein said sample solution is saturated with said oxygen during said period.

* * * * *